(12) United States Patent
Molina Sampayo et al.

(10) Patent No.: US 11,518,811 B2
(45) Date of Patent: Dec. 6, 2022

(54) HUMAN ANTIBODY AND FRAGMENTS THEREOF FOR USE IN THE TREATMENT OF GASTRIC CANCER (GC) AND OTHER TYPES OF TUMOURS EXPRESSING THE MICA PROTEIN (MHC CLASS I CHAIN-RELATED PROTEIN A GENE)

(71) Applicant: Universidad de Chile, Santiago (CL)

(72) Inventors: María Carmen Molina Sampayo, Santiago (CL); Juan Carlos Aguillón Gutierrez, Santiago (CL); Carolina Hager Ribeiro, Santiago (CL); Roberto Aquiles Zúñiga Olate, Santiago (CL); Norberto Andrés Collazomuñoz, Santiago (CL); Lorenzo Leiva Araya, Santiago (CL); Matías Fernando Gutierrez Gonzalez, Santiago (CL); Jaime Camilo Teneb Lobos, Santiago (CL); Alfonso Enrique Romero Trujillo, Santiago (CL); Bastían Nicolás Jerez Donoso, Santiago (CL)

( * ) Notice: Subject to any disclaimer, the term of this patent is extended or adjusted under 35 U.S.C. 154(b) by 76 days.

(21) Appl. No.: 16/959,096

(22) PCT Filed: Dec. 27, 2018

(86) PCT No.: PCT/CL2018/050151
§ 371 (c)(1),
(2) Date: Jun. 29, 2020

(87) PCT Pub. No.: WO2019/126895
PCT Pub. Date: Jul. 4, 2019

(65) Prior Publication Data
US 2021/0139593 A1    May 13, 2021

(30) Foreign Application Priority Data
Dec. 29, 2017   (CL) .................................. 3503-2017

(51) Int. Cl.
*C07K 16/00*    (2006.01)
*C07K 16/28*    (2006.01)
*G01N 33/574*   (2006.01)

(52) U.S. Cl.
CPC ...  *C07K 16/2833* (2013.01); *G01N 33/57492* (2013.01); *C07K 2317/21* (2013.01); *C07K 2317/35* (2013.01); *C07K 2317/524* (2013.01); *C07K 2317/526* (2013.01); *C07K 2317/55* (2013.01); *C07K 2317/56* (2013.01); *C07K 2317/565* (2013.01); *C07K 2317/622* (2013.01)

(58) Field of Classification Search
CPC ............ C07K 16/2833; C07K 2317/21; C07K 2317/35; C07K 2317/524; C07K 2317/526; C07K 2317/55; C07K 2317/56; C07K 2317/565; C07K 2317/622; G01N 33/57492
See application file for complete search history.

(56) References Cited

FOREIGN PATENT DOCUMENTS

| WO | 2016090278 A2 | 9/2016 |
|---|---|---|
| WO | 2016166139 A1 | 10/2016 |
| WO | 2017157895 A1 | 9/2017 |

OTHER PUBLICATIONS

International Search Report issued in connection with PCT Application No. PCT/CL2018/050151 dated Apr. 29, 2019.
Sotelo, P.H. et al, "An efficient method for variable region assembly in the construction of scFv phage display libraries using independent strand amplification." MAbs. Taylor & Francis, 2012. vol. 4, No. 4, p. 542-550.
Zhang B., et al. "The inhibitory effects of 1-9 synthetic short peptides, mimicking MICA and targeting at NKG2D receptors, on function of NK cells," Peptides, Elsevier, Amsterdam, NL, vol. 26, No. 3, Mar. 1, 2005, pp. 405-412.
Yizhou Zou et al. "Polymorphisms of MICA recognized by human alloantibodies", Immunogenetics, Springer, Berlin, De, vol. 61, No. 2, Dec. 10, 2008, pp. 91-11.
Supplemental European Search Report issued in connection with Application No. EP 18894287 dated Jul. 23, 2021.
Jian-jun Li et al. "Prognostic value of soluble MICA levels in the serum of patients with advanced hepatocellular carcinoma", Atzheng Chinese Journal of Cancer, vol. 32, No. 3, Mar. 5, 2013, pp. 141-148.

*Primary Examiner* — Lei Yao
(74) *Attorney, Agent, or Firm* — Dennemeyer & Associates; Victoria Friedman

(57) ABSTRACT

A bivalent, anti-MICA human monoclonal antibody formed by two or more heavy and light chains with a variable immunoglobulin domain neutralises the MICA protein in its soluble state and opsonises tumour cells expressing the antigen, stimulating adaptive immunity in the treatment of gastric cancer or other types of cancer in which the tumour cells express MICA in the soluble form or abundantly on their surface.

14 Claims, 2 Drawing Sheets
Specification includes a Sequence Listing.

AGS

MKN

HUMAN ANTIBODY AND FRAGMENTS THEREOF FOR USE IN THE TREATMENT OF GASTRIC CANCER (GC) AND OTHER TYPES OF TUMOURS EXPRESSING THE MICA PROTEIN (MHC CLASS I CHAIN-RELATED PROTEIN A GENE)

FIELD OF THE INVENTION

The developed invention corresponds to a fully human bivalent anti-MICA antibody, heterodimer, consisting of two variable domains contained in separate peptide chains, a heavy chain and a light chain, and/or homodimer, consisting of two variable domains contained in a single peptide chain linked by a linker peptide (scFv), linked to the immunoglobulin CH2 and CH3 domains. These monoclonal antibodies were designed to specifically bind to the MICA a1 subunit. Functionally, it is capable of binding to the MICA protein in its soluble state, and it is capable of binding to tumour cells expressing the MICA antigen, thereby activating the effector functions of the antibodies, allowing the tumour cells that express the MICA antigen to be opsonised, activating the system of the complement and inducing its cellular cytolysis through CD16 (ADCC) or facilitating apoptotic tumour cell phagocytosis by dendritic cells. Additionally, by inactivating the antigen by one of the two mechanisms, it reverses the inactivation of NK cells against these tumours, stimulating anti-tumour immunity.

SEQUENCE LISTING INCORPORATION

Biological sequence information for this application is included in an ASCII text file, having the file name "20180203_273146_SequenceListing.txt", created on Sep. 14, 2020, and having a file size of 18,199 bytes which is incorporated herein by reference.

BACKGROUND

The present invention consists of a monoclonal antibody that binds to the MICA protein for the treatment of diseases in which it is desirable to regulate the expression of this protein, such as gastric cancer or other cancers that express it in soluble form or in high concentrations on the surface of tumour cells. The invention is based on novel monoclonal antibodies directed against the MICA a1 subunit, in its soluble state as well as in its state linked to the membrane of tumour cells. It specifically binds to the a1 subunit peptide of MICA SEQ ID NO: 1. These antibodies are defined by their heavy- and light-chain variable regions (or variable domains), which are described in the present application. The invention also comprises pharmaceutical compositions containing the monoclonal antibody to be used in the treatment of gastric cancer or other cancers in which the cells express MICA in the soluble form or abundantly on their surface. In order to better illustrate the invention, the present document describes the present invention considering some cases in which it can be applied; however, these examples should not be considered as limiting the invention.

Gastric cancer is the leading cause of cancer-related death worldwide, with an average of less than twelve months of survival when cancer is diagnosed in advanced stages. Overexpression of MICA has been observed in the epithelium of patients with this type of cancer. However, this ligand can be released from the surface of transformed cells, and in its soluble form, it is capable of binding to the receptor activator of natural "killer" cells or naturally cytolytic (NK) cells, the D member of group 2 (NKG2D), a type 2 transmembrane receptor, related to lectins. This effect causes said receptors to be saturated with the soluble MICA ligand, resulting in them not being able to efficiently recognise the MICA ligand present in the tumour cells. Furthermore, the release of MICA from the surface of the tumour cells causes a decrease in the density of these ligands, generating a decrease in the recognition of the tumour cells by natural "Killer" cells. Both effects favour tumour progression in this type of cancer. This is why the need to develop agents that block/decrease MICA activity in patients who have been diagnosed with gastric cancer has recently been recognised.

There are commercially available immunogenic preparations and monoclonal antibodies that bind to MICA, which are described as useful in inhibiting the proliferation of cancer cells. To assess the merits of the invention described herein, a brief summary of the most relevant documents known in the prior art is presented. One of the most relevant documents is WO2015179627A1, which discloses a method for treating or alleviating cancer patients by means of which an antibody directed against the soluble version of the MICA antigen is used. However, the patent application discloses a method without describing the structure of the antibodies developed in said invention. WO2017157895A1 describes antigen binding proteins and antibodies that bind to MICA polypeptides, which are defined by the heavy- and light-chain variable regions, but only the use thereof to bind to the MICA antigen expressed in target cells is claimed, and they are not indicated for use for binding to soluble MICA.

BRIEF DESCRIPTION OF THE INVENTION

The invention corresponds to a fully human antibody, formed by two heavy chains with variable domain and constant domains, and by two light chains with variable domain and constant domain, or formed by two chains with four immunoglobulin domains; one variable domain of the heavy chain, one further domain of the light chain, linked by a simple chain (scFv), and the CH2 and CH3 domains of immunoglobulin constant regions, which specifically bind to the MICA a1 subunit and which are defined at structure level. Monoclonal antibodies possess a heavy-chain variable region SEQ ID NO: 2 and have a light-chain variable region SEQ ID NO: 3. The embodiment of the invention has several possibilities. Among these are nucleic acids, vectors, cells, compositions, methods and uses of the antibodies developed in the present invention to be used in the treatment of cancers that overexpress MICA, including gastric.

DETAILED DESCRIPTION OF THE INVENTION

Figure 1:
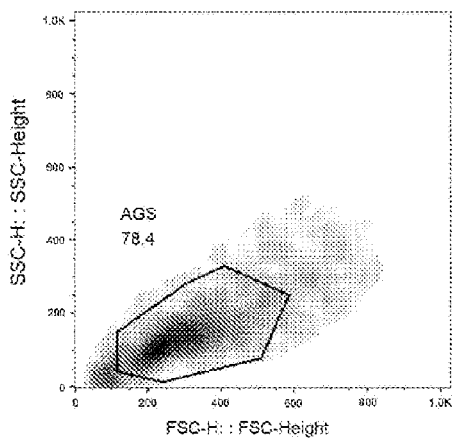
FIG. 1. Detection of scFv binding by native MICA. AGS (A) and MKN-45 (B) gastric cancer lines were incubated with a commercial anti-MICA antibody or anti-MICA scFv (2 h, 37° C.). After rinsing, the cells were incubated with mouse anti-IgG conjugated to FITC, those treated with commercial antibody, and anti-HA epitope murine antibody and then mouse anti-IgG antibody conjugated to FITC, those treated with commercial antibody, and anti-HA epitope murine antibody, and then mouse anti-IgG antibody conjugated to FITC. The binding of the anti-MICA scFv to native MICA was analysed by flow cytometry, using the AGS gastric cancer lines (upper panel) and MKN gastric cancer lines (lower panel). In the left panels, the population used for the analysis is shown and, on the right side, the FITC signal of unlabeled cells (light grey, solid line), cells labelled with a commercial anti-MICA antibody conjugated to FITC (grey, dotted line), and the scFv signal, detected with an anti-HA antibody conjugated to FITC (black, solid line), are shown. The average fluorescence in the FL1-H channel is shown in the table below.
Figure 1:
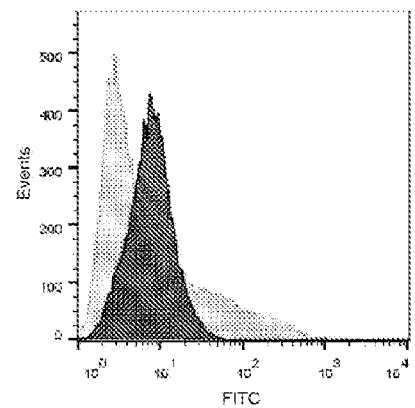
Figure 1:
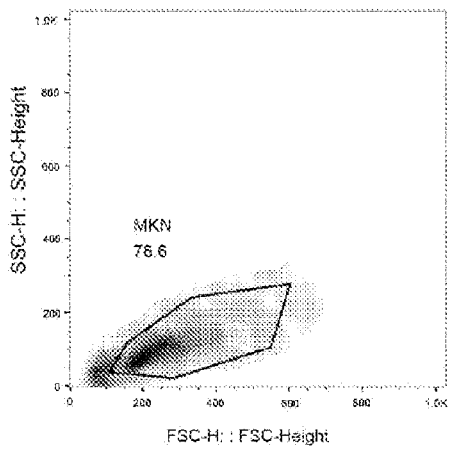
Figure 1:
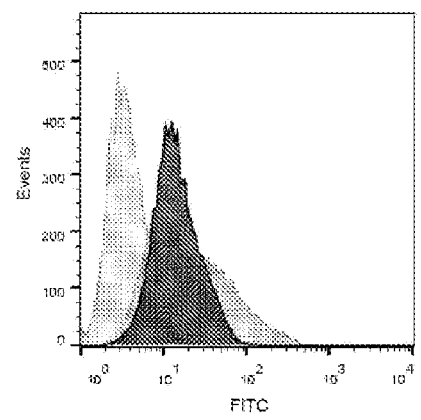
Figure 2:
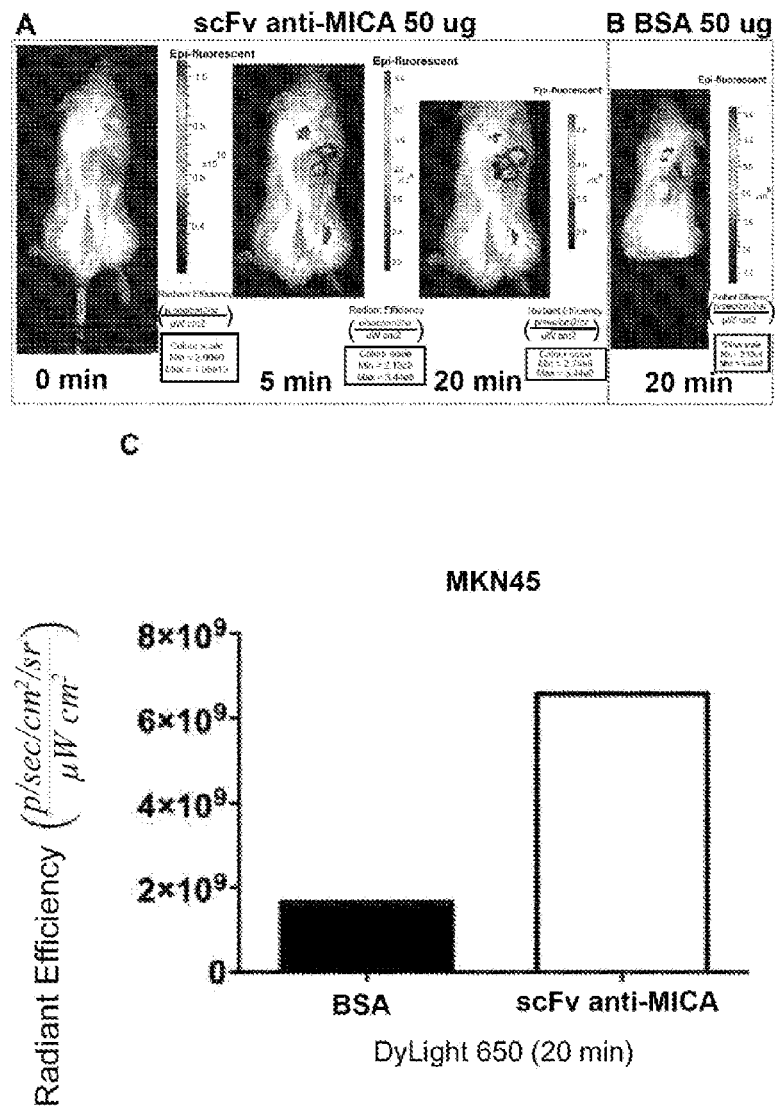
FIG. 2. Fluorescence emission in NOD-SCID-IL-null (or NSG) mice with MKN-45 cell tumour. Mice inoculated subcutaneously with 1×100 MKN-45 gastric adenocarcinoma cells, once the tumour was established on day 60, were intravenously (lateral tail vein) injected with 50 pg of scFv-MICA conjugated to DyLight 650. As a negative control of tumour binding, 50 pg bovine serum albumin (BSA) conjugated to DyLight 650 was used. The mice were intramuscularly anesthetised with a ketamine:xylazine mixture in a 100:10 v:v ratio, once anesthetised, the fluorescence emission in the tumour area was analysed using LUMINA II IN/IS (In Vivo Imaging Systems). (A) scFv-MICA-DyLight 650 fluorescence emission, 0, 5 and 20 minutes approximately post-inoculation. (B) BSA-DyLight 650 fluorescence emission, approximately 20 minutes post-inoculation. (C) fluorescence emission difference between conjugated BSA and conjugated scFv-MICA approximately 20 minutes post-inoculation. In Figure A, the thoracic region shows two signals: an upper one, which corresponds to the heart and a lower one, which corresponds to the tumour. Both signals are seen at 5 and 20 min post-inoculation; however, it is seen that the signal from the heart is lower at 20 minutes, while the signal from the tumour is higher, indicating that there is accumulation of scFv-MICA-DyLight 650 in the latter.

The invention corresponds to fully human bivalent monoclonal antibodies which specifically bind to the MICA a1 subunit, SEQ ID NO: 1, which comprise a heavy-chain variable domain SEQ ID NO: 2 and comprise a light-chain variable domain SEQ ID NO: 3.

In a specific preferred embodiment, the antibodies are bivalent of a scFv-Fc-type chain (wherein scFv is an antibody fragment consisting of a heavy-chain variable domain and a light-chain variable domain contained in a heavy chain, and a light-chain variable domain contained in a single peptide chain linked via a chorus peptide linker (SEQ ID NO: 12, Linker 1 and SEQ ID NO: 13 Linker 2) formed by the fusion of anti-MICA scFv (SEQ ID NO: 14) with the CH2 and CH3 domain of human gamma 1 immunoglobulin (SEQ ID NO: 15) and/or bivalent two-Fab-type-chain antibodies, i.e. the separate peptide chains linked by non-covalent interactions, wherein the light chain contains the human Kappa immunoglobulin CH1 domain (SEQ ID NO: 16) and the heavy chain contains the CH1, CH2 and CH3 domains of human gamma 1 immunoglobulin (SEQ ID NO: 17).

In a preferred embodiment of the invention it comprises nucleic acid sequences, which code for the heavy-chain variable domain (SEQ ID NO: 4) and the light-chain variable domain (SEQ ID NO: 5).

In a more specific embodiment, the antibody or fragments thereof according to the present invention comprises CDR complementarity determining regions in accordance with the following definitions: CDR-L1: described in SEQ ID NO: 6; CDR-L2: described in SEQ ID NO: 7; CDR-L3: described in SEQ ID NO: 8; CDR-H1: described in SEQ ID NO: 9; CDR-H2: described in SEQ ID NO: 10; CDR-H3: described in SEQ ID NO: 11.

In a preferred embodiment, the invention relates to pharmaceutical compositions comprising monoclonal antibodies and a pharmaceutical^ acceptable carrier.

In a preferred embodiment, the invention relates to a method for detecting the soluble MICA factor in a sample, wherein the method comprises the following steps: (a) taking the sample from a patient, from blood or tumour cell culture supernatant; (b) placing the sample in contact with 0.3 micrograms of developed monoclonal antibody, fixed to a microtitration plate; (c) incubating the sample with a secondary commercial anti-MICA antibody conjugated to peroxidase; and (d) quantifying the concentration of the soluble factor by means of a colorimetric signal, after adding the enzyme substrate, in a spectrophotometer.

In another preferred embodiment, the invention relates to a kit which comprises a pharmaceutical composition made with the antibody of the invention, which is stored in a pharmaceutical^ acceptable container.

In another preferred embodiment, the invention relates to a method for therapeutic treatment against cancers selected from the following: hepatocellular carcinoma, melanoma, kidney.

In a more particular preferred embodiment, the cancer is gastric cancer.

EXAMPLES

Example 1: Choice of the Epitope or Segment of the MICA Molecule to which the Recombinant Antibody Will Bind In order to select an epitope, and not leave to chance the site of the molecule against which the antibody would bind, a Multiple Antigen Peptide System (MAPS) was designed, which consists of a nucleus of lysines and 8 arms of the same peptide. For the design of MAPS, the polymorphisms of the MICA protein, its tertiary structure and its binding site with the NKG2D receptor, obtained from the structure of the NKG2D-MICA complex (PDB: 1HYR) were analysed. The least polymorphic MICA alpha helix segment was chosen and the RDLTGNGKDLRMTLAHIKDQ (MICA Alpha1) peptide was generated (SEQ ID NO: 1). Subsequently, a massive sequencing analysis of 50 samples from patients with gastric cancer was performed in the laboratory and no variants were found in this segment. Therefore, this segment was selected for the later stages due to its low polymorphic variability.

Example 2: Selection and Characterisation of a Viral Particle that Expresses Anti-MICA scFv (scFv-aMICA-Phage)

Selection or panning of the viral particle carrying the gene that codes for scFv-aMICA (scFv-aMICA-phage) was performed with the MAPS peptide from a library presenting scFvs on the surface of M13 phage, previously constructed in the laboratory from healthy donors as described in Sotelo et al. (An efficient method for variable region assembly in the construction of scFv phage display libraries using independent strand amplification. mAbs 4, 542-550, doi: 10.4161/mabs.20653 (2012)). After three cycles of panning with the peptide, 70 clones were randomly selected and an ELISA assay was performed, with recombinant MICA-sensitised plates, wherein the peptide and two different proteins blocked the remaining sites of the plate. The clones with the highest signal were selected and their reactivity against recombinant MICA (rMICA) and native MICA was analysed by ELISA and flow cytometry, respectively. The five clones with the highest reactivity against MICA were selected, amplified, and the segments coding for scFv were sequenced. Of these, three had the same sequence and a fourth one had a minor modification, for which reason one of these clones was selected to continue.

Example 3: Generation, Production and Characterisation of the Anti-MICA scFv Protein (scFv-aMICA)

To produce the scFv-aMICA protein, the gene coding for it was subcloned into a variant of the pUCH1 phagemid, called pUCH1 Amber, both constructed in the laboratory. This variant allows independent production of M13 phage capsid components and therefore the purification thereof. It was observed that the molecule maintains its ability to bind to a rMICA and native protein, respectively, by ELISA assay and in vitro culture cytometry of commercial gastric adenocarcinoma cell lines (FIG. 1). Likewise, the anti-MICA scFv, a monomeric molecule, has an affinity constant (KD) of 135±45 nM, Kaff of 7.4±2.5×10® M"$^{1}$. FIG. 3 shows a diagram of the scFv-aMICA model with MICA proposed and subsequently validated in vitro using an animal model of immunosuppressed mice NOD-SCID IL-2Rgnull or NSG 45 (NOD.Cg-Prkdcscid Il2rgtml Wjl/SzJ) (Jackson Laboratories, USA) xenografted with human adenocarcinoma cells (FIG. 2). MICA is a molecule that is absent in mice, thus ensuring the absence of a cross-reaction with molecules from the animal. In this model, it was verified by immunohistochemistry that the human tumour cells, in addition to growing in this murine model, express MICA. Subsequently, fluorescent scFv-aMICA was inoculated (FIG. 2) and it was observed significantly that the scFv-aMICA antibody fragment was located in the tumour unlike fluorescent BSA, its negative control.

The invention claimed is:

1. An isolated monoclonal antibody or antigen binding fragment thereof that specifically binds to the α1 subunit of MICA, SEQ ID NO: 1, wherein said antibody or antigen binding fragment comprises a heavy chain variable domain of SEQ ID NO: 2 and a light chain variable domain SEQ ID NO: 3.

2. The antibody or antigen binding fragment according to claim 1, wherein said antigen binding fragment comprises a scFv formed by a heavy chain variable domain of SEQ ID NO: 2 and a light chain variable domain of SEQ ID NO:3 contained in a single peptide chain linked via a peptide linker selected from SEQ ID NO: 12 and SEQ ID NO: 13.

3. The antibody or antigen binding fragment according to claim 2, wherein said antigen binding fragment comprises CDR-L1 of SEQ ID NO: 6; CDR-L2 of SEQ ID NO: 7; CDR-L3 of SEQ ID NO: 8; CDR-H1 of SEQ ID NO: 9; CDR-H2 of SEQ ID NO: 10; and CDR-H3 of SEQ ID NO: 11.

4. The antibody or antigen binding fragment according to claim 2, wherein said scFv fragment comprises the sequence SEQ ID NO:14.

5. The antibody or antigen binding fragment according to claim 1, wherein said antigen binding fragment is a scFv-Fc type formed by a heavy chain variable domain and a light chain variable domain contained in a single peptide chain linked through a linker peptide selected from SEQ ID NO: 12 and SEQ ID NO: 13 and is fused with the CH2 and CH3 domain of human immunoglobulin gamma-1 consisting of SEQ ID NO: 15.

6. The antibody or antigen binding fragment according to claim 5, wherein said antigen binding fragment comprises CDR-L1 of SEQ ID NO: 6; CDR-L2 of SEQ ID NO: 7; CDR-L3 of SEQ ID NO: 8; CDR-H1 of SEQ ID NO: 9; CDR-H2 of SEQ ID NO: 10; and CDR-H3 of SEQ ID NO: 11.

7. The antibody or antigen binding fragment according to claim 1, wherein said antigen binding fragment comprises CDR-L1 of SEQ ID NO: 6; CDR-L2 of SEQ ID NO: 7; CDR-L3 of SEQ ID NO: 8; CDR-H1 of SEQ ID NO: 9; CDR-H2 of SEQ ID NO: 10; and CDR-H3 of SEQ ID NO: 11.

8. The antibody or antigen binding fragment according to claim 1, wherein said antigen binding fragment comprises heavy chain domain of human immunoglobulin gamma-1 consisting of SEQ ID NO: 17 and light chain domain of human immunoglobulin kappa consisting of SEQ ID NO: 16.

9. A pharmaceutical composition wherein said composition comprises the antibody or antigen binding fragment described in claim 1, and a pharmaceutically acceptable carrier.

10. A pharmaceutical composition wherein said composition comprises the antibody or antigen binding fragment described in claim 2, and a pharmaceutically acceptable carrier.

11. A pharmaceutical composition wherein said composition comprises the antibody or antigen binding fragment described in claim 3, and a pharmaceutically acceptable carrier.

12. A pharmaceutical composition wherein said composition comprises the antibody or antigen binding fragment described in claim 5, and a pharmaceutically acceptable carrier.

13. A pharmaceutical composition wherein said composition comprises the antibody or antigen binding fragment described in claim 7 and a pharmaceutically acceptable carrier.

14. A pharmaceutical composition wherein said composition comprises the antibody or antigen binding fragment described in claim 6, and a pharmaceutically acceptable carrier.

\* \* \* \* \*

SEQUENCE LISTING

<160> NUMBER OF SEQ ID NOS: 17

<210> SEQ ID NO 1
<211> LENGTH: 20
<212> TYPE: PRT
<213> ORGANISM: Homo sapiens

<400> SEQUENCE: 1

Arg Asp Leu Thr Gly Asn Gly Lys Asp Leu Arg Met Thr Leu Ala His
1 5 10 15

Ile Lys Asp Gln
20

<210> SEQ ID NO 2
<211> LENGTH: 132
<212> TYPE: PRT
<213> ORGANISM: Homo sapiens

<400> SEQUENCE: 2

Gln Val Gln Leu Gln Glu Ser Gly Pro Gly Leu Val Lys Pro Ser Gln
1 5 10 15

Thr Leu Ser Leu Thr Cys Thr Val Ser Gly Asp Ser Val Arg Ser Ala
20 25 30

Tyr Ser Ser Trp Asn Trp Ile Arg Gln Pro Pro Gly Lys Gly Leu Glu
35 40 45

Trp Ile Gly Gln Ile His Pro Asn Gly Asn Thr Tyr Tyr Asn Pro Ser
50 55 60

Leu Met Ser Arg Ile Thr Val Ser Ile Asp Thr Ser Lys Asn Gln Phe
65 70 75 80

Ser Leu Lys Leu Asp Ser Val Thr Ala Ala Asp Thr Ala Val Tyr Phe
85 90 95

Cys Ala Thr Glu Gly Val Thr Ser Glu Ser Gly Ser Phe Asp Ile Trp
100 105 110

Gly Gln Gly Arg Met Val Ile Val Ser Ser Ala Ser Thr Lys Gly Pro
115 120 125

Ser Val Ala Ser
130

<210> SEQ ID NO 3
<211> LENGTH: 114
<212> TYPE: PRT
<213> ORGANISM: Homo sapiens

<400> SEQUENCE: 3

Glu Phe Gly Val Val Met Thr Gln Ser Pro Asp Phe Gln Ser Val Thr
1               5                   10                  15

Pro Lys Glu Lys Val Thr Ile Thr Cys Arg Ala Ser Gln Ser Ile Gly
            20                  25                  30

Arg Ser Ile His Trp Tyr Gln Gln Lys Pro Asp Gln Ser Pro Lys Leu
        35                  40                  45

Leu Val Met Tyr Ala Ser Gln Ser Phe Ser Gly Val Pro Ser Arg Phe
    50                  55                  60

Ser Gly Ser Gly Ser Gly Thr Asp Phe Thr Leu Thr Ile Asn Ser Leu
65                  70                  75                  80

Glu Ala Glu Asp Ala Ala Thr Tyr Tyr Cys His Gln Ser Tyr Ser Val
                85                  90                  95

Pro Arg Ser Phe Gly Gln Gly Thr Lys Leu Glu Ile Lys Arg Thr Val
            100                 105                 110

Ala Ala

<210> SEQ ID NO 4
<211> LENGTH: 342
<212> TYPE: DNA
<213> ORGANISM: Homo sapiens

<400> SEQUENCE: 4
gaattcggtg ttgtgatgac tcagtctcca gattttcagt ctgtgactcc aaaggagaag      60
gtcaccatca cctgccgggc cagtcagagc attggtcgta gtatacactg gtaccagcag     120
aaaccagatc agtctccaaa gctcctcgtc atgtatgctt cccagtcctt ctcaggggtc     180
ccctcgaggt tcagtggcag tggatctggg acagatttca ccctcaccat caatagcctg     240
gaagctgaag atgctgcaac gtattactgc catcagagtt atagtgtacc tcggagtttt     300
ggccagggga ccaagctgga gatcaaacga actgtggctg ca                        342

<210> SEQ ID NO 5
<211> LENGTH: 396
<212> TYPE: DNA
<213> ORGANISM: Homo sapiens

<400> SEQUENCE: 5
caggtgcagc tgcaggagtc gggcccagga ctggtgaagc cttcacagac cctgtccctc      60
acctgcactg tctctggtga ctccgtcaga agtgcctatt cctcctggaa ctggatccgg     120
cagccaccag ggaagggcct ggagtggatt gggcagattc atcctaatgg aacacctac      180 tacaacccgt ccctcatgag tcgaatcacc gtgtctatag acacgtccaa gaaccagttt     240
tccctgaagc tggactctgt gaccgccgcg gacacggccg tttatttctg tgccactgag     300
ggtgttacct ccgagtcggg ctcttttgat atctggggcc aaggcagaat ggtcatcgtc     360
tcttcagctt ccaccaaggg cccatcggtc gctagc                               396

<210> SEQ ID NO 6
<211> LENGTH: 11
<212> TYPE: PRT
<213> ORGANISM: Homo sapiens

<400> SEQUENCE: 6

Arg Ala Ser Gln Ser Ile Gly Arg Ser Ile His
1               5                   10

```
<210> SEQ ID NO 7
<211> LENGTH: 7
<212> TYPE: PRT
<213> ORGANISM: Homo sapiens

<400> SEQUENCE: 7

Met Tyr Ala Ser Gln Ser Phe
1               5

<210> SEQ ID NO 8
<211> LENGTH: 9
<212> TYPE: PRT
<213> ORGANISM: Homo sapiens

<400> SEQUENCE: 8

His Gln Ser Tyr Ser Val Pro Arg Ser
1               5

<210> SEQ ID NO 9
<211> LENGTH: 13
<212> TYPE: PRT
<213> ORGANISM: Homo sapiens

<400> SEQUENCE: 9

Gly Asp Ser Val Arg Ser Ala Tyr Ala Ser Ser Trp Asn
1               5                   10

<210> SEQ ID NO 10
<211> LENGTH: 16
<212> TYPE: PRT
<213> ORGANISM: Homo sapiens

<400> SEQUENCE: 10

Gly Ile His Pro Asn Gly Asn Thr Tyr Tyr Asn Pro Ser Leu Met Ser
1               5                   10                  15

<210> SEQ ID NO 11
<211> LENGTH: 12
<212> TYPE: PRT
<213> ORGANISM: Homo sapiens

<400> SEQUENCE: 11

Glu Gly Val Thr Ser Glu Ser Gly Ser Phe Asp Ile
1               5                   10

<210> SEQ ID NO 12
<211> LENGTH: 18
<212> TYPE: PRT
<213> ORGANISM: Artificial Sequence
<220> FEATURE:
<223> OTHER INFORMATION: Linker sequence

<400> SEQUENCE: 12

Gly Gly Ser Ser Arg Ser Ser Ser Ser Gly Gly Gly Gly Ser Gly Gly
1               5                   10                  15

Gly Gly

<210> SEQ ID NO 13
<211> LENGTH: 17
<212> TYPE: PRT
<213> ORGANISM: Artificial Sequence
<220> FEATURE:
<223> OTHER INFORMATION: Linker sequence

<400> SEQUENCE: 13
```

Gly Gly Ser Ala Asp Asp Ala Lys Lys Asp Ala Ala Lys Lys Asp Gly
1               5                   10                  15
Gly

<210> SEQ ID NO 14
<211> LENGTH: 264
<212> TYPE: PRT
<213> ORGANISM: Artificial Sequence
<220> FEATURE:
<223> OTHER INFORMATION: Linker sequence

<400> SEQUENCE: 14

Glu Phe Gly Val Val Met Thr Gln Ser Pro Asp Phe Gln Ser Val Thr
1               5                   10                  15

Pro Lys Glu Lys Val Thr Ile Thr Cys Arg Ala Ser Gln Ser Ile Gly
                20                  25                  30

Arg Ser Ile His Trp Tyr Gln Gln Lys Pro Asp Gln Ser Pro Lys Leu
            35                  40                  45

Leu Val Met Tyr Ala Ser Gln Ser Phe Ser Gly Val Pro Ser Arg Phe
        50                  55                  60

Ser Gly Ser Gly Ser Gly Thr Asp Phe Thr Leu Thr Ile Asn Ser Leu
65                  70                  75                  80

Glu Ala Glu Asp Ala Ala Thr Tyr Tyr Cys His Gln Ser Tyr Ser Val
                85                  90                  95

Pro Arg Ser Phe Gly Gln Gly Thr Lys Leu Glu Ile Lys Arg Thr Val
                100                 105                 110

Ala Ala Gly Gly Ser Ser Arg Ser Ser Ser Gly Gly Gly Gly Ser
            115                 120                 125

Gly Gly Gly Gly Gln Val Gln Leu Gln Glu Ser Gly Pro Gly Leu Val
            130                 135                 140

Lys Pro Ser Gln Thr Leu Ser Leu Thr Cys Thr Val Ser Gly Asp Ser
145                 150                 155                 160

Val Arg Ser Ala Tyr Ser Ser Trp Asn Trp Ile Arg Gln Pro Pro Gly
                165                 170                 175

Lys Gly Leu Glu Trp Ile Gly Gln Ile His Pro Asn Gly Asn Thr Tyr
            180                 185                 190

Tyr Asn Pro Ser Leu Met Ser Arg Ile Thr Val Ser Ile Asp Thr Ser
        195                 200                 205

Lys Asn Gln Phe Ser Leu Lys Leu Asp Ser Val Thr Ala Ala Asp Thr
210                 215                 220

Ala Val Tyr Phe Cys Ala Thr Glu Gly Val Thr Ser Glu Ser Gly Ser
225                 230                 235                 240

Phe Asp Ile Trp Gly Gln Gly Arg Met Val Ile Val Ser Ser Ala Ser
                245                 250                 255

Thr Lys Gly Pro Ser Val Ala Ser
            260

<210> SEQ ID NO 15
<211> LENGTH: 496
<212> TYPE: PRT
<213> ORGANISM: Artificial Sequence
<220> FEATURE:
<223> OTHER INFORMATION: Linker sequence

<400> SEQUENCE: 15

Glu Phe Gly Val Val Met Thr Gln Ser Pro Asp Phe Gln Ser Val Thr
1               5                   10                  15

```
Pro Lys Glu Lys Val Thr Ile Thr Cys Arg Ala Ser Gln Ser Ile Gly
            20                  25                  30

Arg Ser Ile His Trp Tyr Gln Gln Lys Pro Asp Gln Ser Pro Lys Leu
        35                  40                  45

Leu Val Met Tyr Ala Ser Gln Ser Phe Ser Gly Val Pro Ser Arg Phe
    50                  55                  60

Ser Gly Ser Gly Ser Gly Thr Asp Phe Thr Leu Thr Ile Asn Ser Leu
65                  70                  75                  80

Glu Ala Glu Asp Ala Ala Thr Tyr Tyr Cys His Gln Ser Tyr Ser Val
                85                  90                  95

Pro Arg Ser Phe Gly Gln Gly Thr Lys Leu Glu Ile Lys Arg Thr Val
            100                 105                 110

Ala Ala Gly Gly Ser Ser Arg Ser Ser Ser Ser Gly Gly Gly Gly Ser
        115                 120                 125

Gly Gly Gly Gly Gln Val Gln Leu Gln Glu Ser Gly Pro Gly Leu Val
    130                 135                 140

Lys Pro Ser Gln Thr Leu Ser Leu Thr Cys Thr Val Ser Gly Asp Ser
145                 150                 155                 160

Val Arg Ser Ala Tyr Ser Ser Trp Asn Trp Ile Arg Gln Pro Pro Gly
                165                 170                 175

Lys Gly Leu Glu Trp Ile Gly Gln Ile His Pro Asn Gly Asn Thr Tyr
            180                 185                 190

Tyr Asn Pro Ser Leu Met Ser Arg Ile Thr Val Ser Ile Asp Thr Ser
        195                 200                 205

Lys Asn Gln Phe Ser Leu Lys Leu Asp Ser Val Thr Ala Ala Asp Thr
    210                 215                 220

Ala Val Tyr Phe Cys Ala Thr Glu Gly Val Thr Ser Glu Ser Gly Ser
225                 230                 235                 240

Phe Asp Ile Trp Gly Gln Gly Arg Met Val Ile Val Ser Ser Ala Ser
                245                 250                 255

Thr Lys Gly Pro Ser Val Ala Ser Glu Pro Lys Ser Cys Asp Lys Thr
            260                 265                 270

His Thr Cys Pro Pro Cys Pro Ala Pro Glu Leu Leu Gly Gly Pro Ser
        275                 280                 285

Val Phe Leu Phe Pro Pro Lys Pro Lys Asp Thr Leu Met Ile Ser Arg
    290                 295                 300

Thr Pro Glu Val Thr Cys Val Val Asp Val Ser His Glu Asp Pro
305                 310                 315                 320

Glu Val Lys Phe Asn Trp Tyr Val Asp Gly Val Glu Val His Asn Ala
                325                 330                 335

Lys Thr Lys Pro Arg Glu Glu Gln Tyr Asn Ser Thr Tyr Arg Val Val
            340                 345                 350

Ser Val Leu Thr Val Leu His Gln Asp Trp Leu Asn Gly Lys Glu Tyr
        355                 360                 365

Lys Cys Lys Val Ser Asn Lys Ala Leu Pro Ala Pro Ile Glu Lys Thr
    370                 375                 380

Ile Ser Lys Ala Lys Gly Gln Pro Arg Glu Pro Gln Val Tyr Thr Leu
385                 390                 395                 400

Pro Pro Ser Arg Asp Glu Leu Thr Lys Asn Gln Val Ser Leu Thr Cys
                405                 410                 415

Leu Val Lys Gly Phe Tyr Pro Ser Asp Ile Ala Val Glu Trp Glu Ser
            420                 425                 430
```

```
Asn Gly Gln Pro Glu Asn Asn Tyr Lys Thr Thr Pro Pro Val Leu Asp
            435                 440                 445

Ser Asp Gly Ser Phe Phe Leu Tyr Ser Lys Leu Thr Val Asp Lys Ser
450                 455                 460

Arg Trp Gln Gln Gly Asn Val Phe Ser Cys Ser Val Met His Glu Ala
465                 470                 475                 480

Leu His Asn His Tyr Thr Gln Lys Ser Leu Ser Leu Ser Pro Gly Lys
                485                 490                 495
```

<210> SEQ ID NO 16
<211> LENGTH: 216
<212> TYPE: PRT
<213> ORGANISM: Artificial Sequence
<220> FEATURE:
<223> OTHER INFORMATION: Linker sequence

<400> SEQUENCE: 16

```
Glu Phe Gly Val Val Met Thr Gln Ser Pro Asp Phe Gln Ser Val Thr
1               5                   10                  15

Pro Lys Glu Lys Val Thr Ile Thr Cys Arg Ala Ser Gln Ser Ile Gly
            20                  25                  30

Arg Ser Ile His Trp Tyr Gln Gln Lys Pro Asp Gln Ser Pro Lys Leu
        35                  40                  45

Leu Val Met Tyr Ala Ser Gln Ser Phe Ser Gly Val Pro Ser Arg Phe
50                  55                  60

Ser Gly Ser Gly Ser Gly Thr Asp Phe Thr Leu Thr Ile Asn Ser Leu
65                  70                  75                  80

Glu Ala Glu Asp Ala Ala Thr Tyr Tyr Cys His Gln Ser Tyr Ser Val
                85                  90                  95

Pro Arg Ser Phe Gly Gln Gly Thr Lys Leu Glu Ile Lys Arg Thr Val
            100                 105                 110

Ala Ala Ala Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215
```

<210> SEQ ID NO 17
<211> LENGTH: 452
<212> TYPE: PRT
<213> ORGANISM: Artificial Sequence
<220> FEATURE:
<223> OTHER INFORMATION: Linker sequence

<400> SEQUENCE: 17

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Asp Ser Val Arg Ser Ala
            20                  25                  30
```

Tyr Ser Ser Trp Asn Trp Ile Arg Gln Pro Pro Gly Lys Gly Leu Glu
         35                  40                  45

Trp Ile Gly Gln Ile His Pro Asn Gly Asn Thr Tyr Tyr Asn Pro Ser
 50                  55                  60

Leu Met Ser Arg Ile Thr Val Ser Ile Asp Thr Ser Lys Asn Gln Phe
 65                  70                  75                  80

Ser Leu Lys Leu Asp Ser Val Thr Ala Ala Asp Thr Ala Val Tyr Phe
                 85                  90                  95

Cys Ala Thr Glu Gly Val Thr Ser Glu Ser Gly Ser Phe Asp Ile Trp
            100                 105                 110

Gly Gln Gly Arg Met Val Ile Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

```
Met His Glu Ala Leu His Asn His Tyr Thr Gln Lys Ser Leu Ser Leu
        435                 440                 445
Ser Pro Gly Lys
    450
```